United States Patent [19]

Butterworth et al.

[11] Patent Number: 5,326,616
[45] Date of Patent: Jul. 5, 1994

[54] LASER-PROTECTION SURGICAL DRAPE

[75] Inventors: David Butterworth, Colleyville; Joseph Salvatore, Arlington, both of Tex.

[73] Assignee: Johnson & Johnson Medical, Inc., Arlington, Tex.

[21] Appl. No.: 880,795

[22] Filed: May 8, 1992

[51] Int. Cl.$^5$ .................................. B32B 3/10
[52] U.S. Cl. ........................... 428/131; 128/849; 128/853; 428/212; 428/213; 428/344; 428/450; 428/457
[58] Field of Search ........... 128/894, 849, 853, 207.14; 428/457, 459, 213, 212, 344, 450, 131

[56] References Cited

U.S. PATENT DOCUMENTS

| | | | |
|---|---|---|---|
| 4,601,286 | 7/1986 | Kaufman | 128/894 |
| 4,604,998 | 8/1986 | Bellina | 128/849 |
| 4,715,366 | 12/1987 | Teeple | 128/132 |
| 5,014,723 | 5/1991 | Kaufman | 128/853 |
| 5,103,816 | 4/1992 | Kirschbaum et al. | 128/207.14 |
| 5,151,095 | 9/1992 | Teeple, Jr. | 606/2 |

FOREIGN PATENT DOCUMENTS

WO91/03377  3/1991  PCT Int'l Appl. ............ B32B 9/00

Primary Examiner—Paul J. Thibodeau
Assistant Examiner—David Abraham

[57] ABSTRACT

A multi-layer article to protect a patient from laser radiation during surgery comprises two metallic layers sandwiching a flame-resistant, radiation absorbing layer. The facing surfaces of the metallic layers, adjoining the middle layer, are reflective. The top surface of the upper metallic layer has a non-reflective, flame-resistant coating. The radiation-absorbing layer is preferably a hydrogel. The lower metallic layer is preferably thicker than the upper layer and/or is of a metal that has a higher melting temperature than that of the upper layer. The article protects the patient by harmlessly dissipating the energy in a misdirected laser beam for a period of time that will permit a healthcare worker to take corrective action.

20 Claims, 3 Drawing Sheets

Example 3  −25 μm AL distal + 25 μm AL proximal
Example 4  −38 μm AL distal + 25 μm AL proximal
Example 5  −25 μm Cu distal + 25 μm AL proximal

LASER-PROTECTION SURGICAL DRAPE

BACKGROUND OF THE INVENTION

1. Field of the Invention

This invention relates to an article, such as a drape, worn by a patient for protection from stray radiation during laser surgery.

2. Description of the Related Art

Lasers are finding ever increasing use in medical and dental applications. They are being used by ophthalmologists, dermatologists, obstetrician/gynecologists, dentists, and others in "traditional" open surgery, endoscopic surgery, and non-surgical procedures. Lasers have found application in hemostasis, tissue welding and cutting, tissue ablation, photodynamic therapy, etc. With the increasing use of lasers in medical procedures comes a corresponding increase in the need for protection from the potentially harmful effects of stray radiation. If a laser beam that is intended to be directed to a surgical site is instead misdirected, there is risk of harm to the patient as well as to healthcare workers. The harm can be caused either directly, for example, laser-caused burns, or indirectly, if the laser beam strikes a flammable article. A number of drapes and other articles have been developed to protect against these risks.

U.S. Pat. No. 4,601,286, issued Jul. 22, 1986, to J. W. Kaufman, discloses a surgical drape for protecting healthy tissue from damage due to laser exposure during surgery. The drape comprises an adhesive-backed hydrogel layer. In another embodiment of the drape, an adhesive-backed hydrogel layer and a second layer of hydrogel sandwich a metallic sheet. In each case, the adhesive permits the drape to be adhered to the patient. Drapes of the first embodiment withstand laser exposure for only a rather short period of time. Drapes of the embodiment that include the metallic sheet tend to quickly reflect laser radiation, endangering healthcare workers.

U.S. Pat. No. 4,604,998, issued Aug. 12, 1986, to J. H. Bellina, discloses a multi-layered drape to protect a patient during laser surgery. The drape has a non-metallic layer laminated to the top, blackened surface of a first metallic layer. A second metallic layer is separated from the first metallic layer by an air gap. A laser beam enters the drape through the laminated layers and is repeatedly reflected between the facing surfaces of the two metallic layers. A shortcoming of the drape is the difficulty of maintaining the air space between the facing metallic layers.

U.S. Pat. No. 4,014,723, issued May 14, 1991, to J. W. Kaufman, discloses two-layer laser protection article that consists of a xerogel, on the side proximal to the laser beam, and a non-reflective metallic layer on the distal side. In tests, drapes made in accordance with the specification prevented potentially harmful reflection of laser radiation for only a brief period of exposure.

SUMMARY OF THE INVENTION

In accordance with the present invention, a multi-layer article to provide protection from laser radiation during medical procedures comprises:
a) a first metallic layer having a top reflective surface to be placed proximal to a source of laser radiation and a bottom surface to be placed distal from the laser source,
b) a flame-resistant, radiation-absorbing layer having a bottom surface adjacent to the top surface of the first metallic layer, and
c) a second metallic layer having
 i) a reflective bottom surface adjacent to the top surface of the radiation-absorbing layer and
 ii) a top surface having a non-reflective, flame-resistant coating.

The multi-layer article of the present invention provides enhanced protection from misdirected laser radiation both to laser surgery patients and to healthcare workers.

BRIEF DESCRIPTION OF THE DRAWINGS

FIG. 5 is a graph that compares the effectiveness of three different metal layers in protecting against laser drape burn-through.

DETAILED DESCRIPTION OF THE INVENTION

The present invention is intended to protect patients, as well as healthcare workers, from exposure to stray or misdirected laser radiation during laser surgery and other medical procedures. (For convenience and brevity, we sometimes refer to all these procedures as "surgery"). Such protection is needed because laser beams, which can be used to cut and cauterize tissue, are not as easy to control as are the traditional mechanical devices, such as scalpels, that accomplish similar results. The problem is complicated by the fact that some lasers used in medical procedures emit radiation that is beyond the visible range, so that the laser beam cannot be seen directly. For example, the radiation emitted by $CO_2$ lasers is at 10.6 $\mu$m in the infrared. Thus, there is a need to protect the patient from laser exposure outside the area of intended surgery, a need to protect healthcare workers from being exposed to laser radiation reflected from the vicinity of the surgical site, and a need to prevent the laser beam from contacting flammable articles.

Protecting the patient from unwanted exposure requires an article—which, for convenience, we refer to as a "drape"—that blocks the laser radiation and dissipates the energy for a sufficient period to permit corrective action to be taken. For example, if a laser is inadvertently fired, while aimed at a patient, the laser-protection drape must block the radiation long enough to identify the problem and turn off the laser—typically about 5 to 15 seconds. During that period, the drape must also avoid reflecting the beam into the surrounding area, where healthcare workers could suffer injurious exposure. Finally, the drape must not burn.

Figure 1:
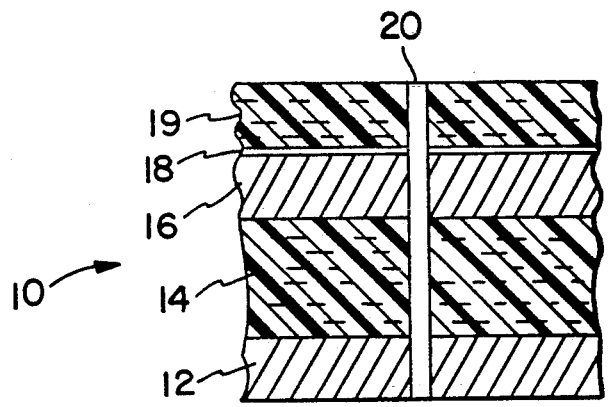
FIG. 1 is a cross-sectional view of a laser drape of the present invention.

FIG. 1 depicts a cross section of a laser-protection drape of the present invention. Multi-layer drape 10 comprises a first metallic layer 12 for placement proximal to the body of a laser surgery patient. Above this layer is a flame-resistant layer 14 that absorbs radiation of the wavelength emitted by the laser. This flame-resistant absorbent layer is preferably a hydrogel. Overlying this layer is a second metallic layer 16, having a non-reflective, flame-resistant coating 18. Reflectance from coating 18 can be reduced by roughening its surface. Instead of, or in addition to, that, a hydrogel layer 19 can overlie the coating to further reduce reflectance. Optional hole 20 permits laser exposure of a surgical site through the drape. Hole 20 is preferably about the same size as the region on a patient over which the surgery is to be performed. Either or both metallic layers may comprise more than one layer to make the drape more flexible and reduce the danger posed by pinholes, for example.

Figure 2:
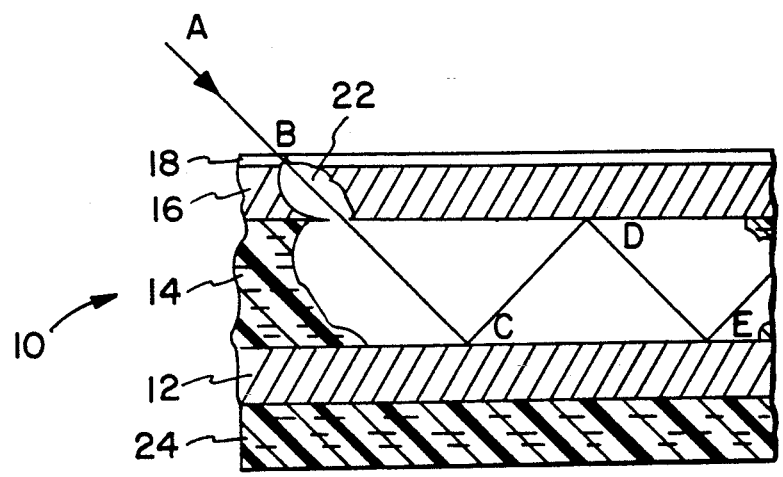
FIG. 2 depicts a cross section of another embodiment of the present drape, showing the effect of a laser beam.

The manner of operation of the present laser-protection article is believed to be as shown in FIG. 2 and described below. Note that optional layer 19 and optional hole 20 have been omitted in the embodiment depicted in FIG. 2. Errant laser beam A impinges on drape 10 at point B. As energy from the laser beam is converted into heat in non-reflective coating 18, the coating and underlying metallic layer 16 get hot in the vicinity of point B. Before coating 18 is vaporized to any substantial extent, layer 16 reaches its melting temperature, causing a hole 22 to form and permitting the laser beam to enter the flame-resistant absorbent layer 14, where part of the beam is absorbed and its energy converted to heat. The transmitted beam is repeatedly reflected at points C, D, E, etc. The edges of the article may be folded over to prevent the escape of the laser beam. Optionally, light diffusing material can be dispersed in layer 14 and/or the top surface of metallic layer 12 can be embossed to disperse the laser beam in layer 14.

When layer 14 is a hydrogel, the beam energy that is absorbed ablates the gel and converts the water of the gel to steam. Steam can exit from entrance hole 22 and from the sides of the article, thereby dissipating heat to the surroundings. Both metallic layers heat up. Heat from metallic layer 16 is dissipated, in part, through coating 18 into the surrounding air. In the embodiment shown in FIG. 2, heat from metallic layer 12 is dissipated, in part, into optional layer 24. Layer 24 may serve as an adhesive to adhere the article to the skin of a patient, or as an insulator, to protect the patient from burns, or as both an adhesive and insulator.

The mechanism described above, by which the energy in the laser beam is converted into heat and is harmlessly dissipated, permits corrective action to be taken. However, if such action is not taken, then the laser energy will ultimately form an exit hole. Preferably the exit hole forms in metallic layer 16 and coating 18, so that the beam does not impinge on the patient. To accomplish that failure mode, the melting temperature of the first metallic layer 12 is preferably higher than that of the second metallic layer 16. Alternatively, layer 12 simply has a greater thickness than layer 16. The materials for layers 12 and 16 may be any suitable metal with a reflective surface, such as aluminum, copper, tin, titanium, iron, etc. Aluminum is a preferred metal, because it is widely available, highly reflective, flexible, corrosion resistant, etc. If layer 16 is aluminum and layer 12 is copper, then layer 16 will have a desirably lower melting temperature to provide the preferred failure mode described above.

The purpose of absorbent layer 14 is to dissipate the laser energy safely. Besides being flame-resistant the layer must absorb the laser radiation. Since the various lasers used in medicine emit radiation of different wavelengths, the ideal material for layer 14 depends on the laser to be used. A commonly used medical laser is a $CO_2$ laser, for which absorbent layer 14 is preferably a hydrogel. High water content is preferred, because water absorbs strongly at 10.6 $\mu$m. A hydrogel that is 96% water and 4% polyethylene oxide is suitable. For lasers that emit in the visible spectrum, hydrogels to which appropriate absorbent dyes have been added work well. Non-reflective coating 18 must be flame resistant. In particular, it must withstand temperatures at least as high as the melting temperature of the metallic layer 16 which it overlies. Thus, metallic layer 16 preferably melts before coating 18 is vaporized, to avoid appreciable reflection of the laser beam into the surrounding area. A preferred paint that satisfactorily resists high temperatures is silicone paint, such as Code 80 or Code 81 Stove Paint, available from Rutland Products, Rutland, Vt.; or #10-901 silicone paint available from Toledo Paint and Chemical Co., Toledo, Ohio. Optional layer 24 may be any medical adhesive known in the art for removably adhering articles to the skin. Alternatively, it may be a thermal insulator. Hydrogels are preferred materials for layer 24, because they can act as an insulator and adhesive both. When the drape is to contact a part of the patient's body that is particularly heat sensitive, such as the eyes, then a better insulator, such as foam or fabric, is preferred.

Figure 3:
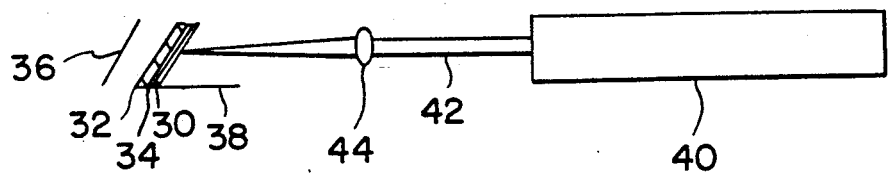
FIG. 3 is a schematic of an experimental setup for testing laser drape performance.

The performance of the present drape was compared with that of drapes of the prior art using an experimental setup depicted in FIG. 3. A drape sample to be tested was cut to a 7.6 cm×7.6 cm square 30 and taped to a 10.2 cm×10.2 cm metal frame 32, which had a central 3.8 cm×3.8 cm square opening. On top of the metal frame was fixed a 0.16 cm thick piece of Teflon ® 34 having the same configuration as the frame. This acted as a thermal barrier to prevent the frame from acting as a heat sink. The central square opening allows beams that pass through a sample to pass through the frame, too. A small sheet of yellow paper 36 was adhered to the back of the metal frame over this opening. If a beam passed through a sample the paper immediately showed a brown spot or a hole or would ignite. The mounted samples were positioned at a 45° angle to the incident laser beam. Another sheet of yellow paper 38 was adhered to the bottom of the sample parallel to the laser beam. When a beam was either reflected off a sample or escaped from a sample by burning through an upper metallic layer, the beam wound create a brown spot or a hole on this paper or would ignite it. The laser source 40 was a Synrad Duo-Lase TM 50W $CO_2$ laser. The laser beam 42 was focused onto the sample 30 with a lens 44 to a 0.27 mm diameter spot, as measured by an aperture procedure (86% of power passing through). Laser power was calibrated using a Molectron Power Max 5100 power meter.

Three power levels were used in the evaluation, 10 watts (the lowest power the laser would produce), 25 watts (to represent a moderate power), and 50 watts (the highest power the laser would produce). The resulting power densities at these three wattages were 17,500, 43,700, and 87,400 watts/cm$^2$, respectively. Five replicates were made for each sample at each power setting (except for Test 3, where ten replicates were made, all at 50 watts power, because all the samples provided substantial protection). If no failure occurred within 240 seconds the trial was discontinued.

Three sets of comparative tests were run and results compared within each test. The sample constructions and the results are described in the Examples below, with the parameters being compared underlined. The element of a sample construction that is listed first is most distal to the laser beam, those that follow are increasingly proximal to the laser beam. In each case the hydrogel was 96% water and 4% polyethylene oxide.

Test 1

EXAMPLE 1PA (Prior Art)

Sample Construction—38 μm Al+150 μm hydrogel

EXAMPLE 1

Sample Construction—38 μm Al+150 μm hydrogel+25 μm Al coated with black silicone paint.

Comparative Results—laser beam promptly reflected at all power levels for Example 1PA but not for Example 1.

Test 2

EXAMPLE 2PA (Prior Art)

Sample Construction—38 μm Al+150 μm air space+2.5 μm Al coated with black silicone paint (effective target is 3.8 cm diameter circle centered in the 76 cm×76 cm square)

EXAMPLE 2

Sample Construction—38 μm Al+150 μm hydrogel+25 μm Al coated with black silicone paint (effective target is 3.8 cm diameter circle centered in 76 cm×76 cm square)

Figure 4:
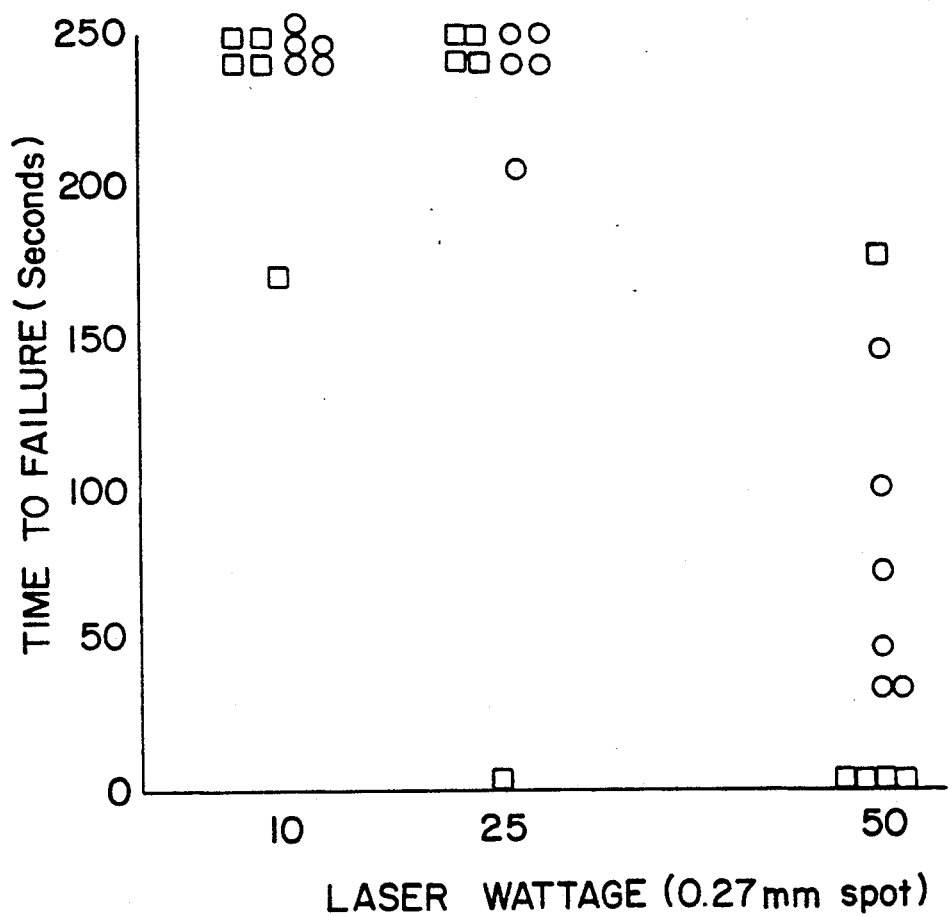
FIG. 4 is a graph that compares the effectiveness of a hydrogel and an air space in absorbing laser radiation.

Comparative Results—As shown In FIG. 4, the sample construction of Example 2 provided better laser protection at high power levels.

Test 3

EXAMPLE 3

Sample Construction—25 μm Al+150 μm hydrogel+25 μm Al coated with black silicone paint.

EXAMPLE 4

Sample Construction—38 μm Al+150 μm hydrogel+25 μm Al coated with black silicone paint (same as Example 1).

EXAMPLE 5

Sample construction—25 μm Cu+150 μm hydrogel+25 μm Al coated with black silicone paint.

Figure 5:
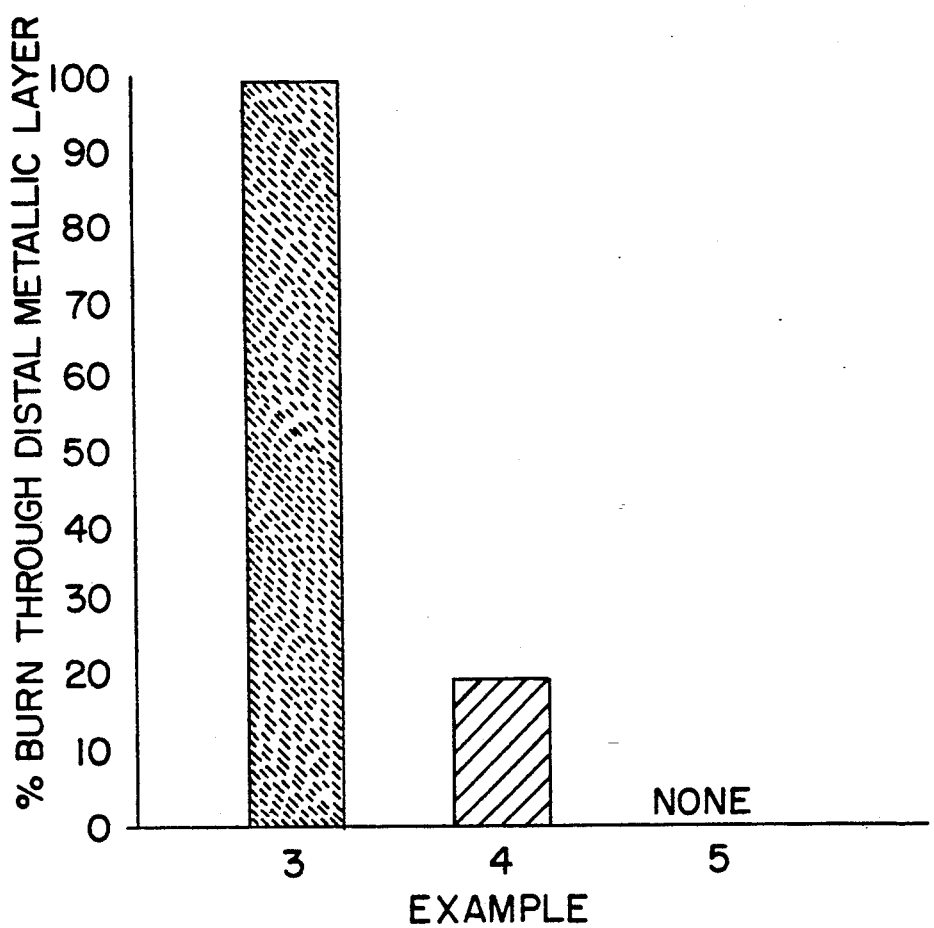

Comparative results—As shown in FIG. 5, having a first metallic layer that is 50% thicker than the second metallic layer reduces failure of the first metallic layer. Having the first metallic layer of a higher melting temperature metal (copper vs. aluminum) reduces failure of the metallic layer even more.

I claim:

1. A multi-layer article to provide protection from laser radiation during medical procedures, comprising:
   a) a first metallic layer having a top reflective surface to be placed proximal to a source of laser radiation and a bottom surface to be placed distal from the laser source,
   b) a flame-resistant, radiation-absorbing layer having a bottom surface adjacent to the top surface of the first metallic layer, and
   c) a second metallic layer having
      i) a reflective bottom surface adjacent to the top surface of the radiation-absorbing layer and
      ii) a top surface having a non-reflective, flame-resistant coating in which the first metallic layer has a thickness that is greater than the thickness of the second metallic layer.

2. A multi-layer article according to claim 1 in which the second metallic layer comprises aluminum.

3. A multi-layer article according to claim 1 in which the radiation-absorbing layer comprises a hydrogel.

4. A multi-layer article according to claim 3 in which the hydrogel comprises about 96% water and about 4% polyethylene oxide.

5. A multi-layer article according to claim 1 further comprising an adhesive coating on the bottom surface of the first metallic layer for adhering to the skin of a patient who is to be protected.

6. A multi-layer article according to claim 1 further comprising an insulating layer on the bottom surface of the first metallic layer.

7. A multi-layer article according to claim 6 in which the insulating layer comprises a hydrogel.

8. A multi-layer article according to claim 1 further comprising means for reducing reflectance from the non-reflective coating.

9. A multi-layer article of claim 8 in which the reflectance-reducing means comprises a hydrogel layer over the non-reflective coating.

10. A multi-layer article according to claim 1 further comprising a fenestration through the layers of the article to permit laser exposure of a surgical site.

11. A multi-layer article to provide protection from laser radiation during medical procedures, comprising:
   a) a first metallic layer having a top reflective surface to be placed proximal to a source of laser radiation and a bottom surface to be placed distal from the laser source,
   b) a flame-resistant, radiation-absorbing layer having a bottom surface adjacent to the top surface of the first metallic layer, and
   c) a second metallic layer having
      i) a reflective bottom surface adjacent to the top surface of the radiation-absorbing layer and
      ii) a top surface having a non-reflective, flame-resistant coating in which the first metallic layer has a melting temperature that is higher than that of the second metallic layer.

12. A multi-layer article according to claim 11 in which the first metallic layer comprises copper and the second metallic layer comprises aluminum.

13. A multi-layer article to provide protection from laser radiation during medical procedures, comprising:
   a) a first metallic layer having a top reflective surface to be placed proximal to a source of laser radiation and a bottom surface to be placed distal from the laser source,
   b) a flame-resistant, radiation-absorbing layer having a bottom surface adjacent to the top surface of the first metallic layer, and
   c) a second metallic layer having
      i) a reflective bottom surface adjacent to the top surface of the radiation-absorbing layer and
      ii) a top surface having a non-reflective, flame-resistant coating in which the non-reflective, flame-resistant coating on the top surface of the second metallic layer has a vaporization temperature higher than the melting temperature of the second metallic layer.

14. A multi-layer article according to claim 13 in which the coating comprises a silicone paint.

15. A multi-layer article according to claim 13 in which the first metallic layer has a thickness that is greater than the thickness of the second metallic layer.

16. A multi-layer article according to claim 13 in which the first metallic layer has a melting temperature that is higher than that of the second metallic layer.

17. A multi-layer article according to claim 13 in which the radiation-absorbing layer comprises a hydrogel.

18. A multi-layer article according to claim 13 further comprising an adhesive coating on the bottom surface of the first metallic layer for adhering to the skin of a patient who is to be protected.

19. A multi-layer article according to claim 13 further comprising an insulating layer on the bottom surface of the first metallic layer.

20. A multi-layer article according to claim 13 further comprising a fenestration through the layers of the article to permit laser exposure of a surgical site.

* * * * *